(12) United States Patent
Alerasool et al.

(10) Patent No.: US 7,279,611 B2
(45) Date of Patent: Oct. 9, 2007

(54) PARAFFIN DEHYDROGENATION CATALYST

(75) Inventors: Saeed Alerasool, Solon, OH (US); Harold E. Manning, Seabrook, TX (US)

(73) Assignee: BASF Catalysts LLC, Florham Park, NJ (US)

( * ) Notice: Subject to any disclaimer, the term of this patent is extended or adjusted under 35 U.S.C. 154(b) by 107 days.

(21) Appl. No.: 11/299,845

(22) Filed: Dec. 12, 2005

(65) Prior Publication Data

US 2006/0094914 A1  May 4, 2006

Related U.S. Application Data

(62) Division of application No. 10/170,297, filed on Jun. 12, 2002, now Pat. No. 7,012,038.

(51) Int. Cl.
*C07C 5/333* (2006.01)
*C07C 5/327* (2006.01)
*C07C 5/32* (2006.01)
*C07C 5/35* (2006.01)
*C07C 5/367* (2006.01)

(52) U.S. Cl. .................. 585/663; 585/630; 585/631; 585/662; 585/445

(58) Field of Classification Search ............... 585/663, 585/660, 631, 662, 445
See application file for complete search history.

(56) References Cited

U.S. PATENT DOCUMENTS

| | | |
|---|---|---|
| 2,943,067 A | 6/1960 | Sieg |
| 2,945,823 A | 7/1960 | Cornelius et al. |
| 2,956,030 A | 10/1960 | Cornelius et al. |
| 3,285,985 A | 11/1966 | Kline et al. |
| 3,781,375 A | 12/1973 | Shima et al. |
| 3,931,348 A | 1/1976 | Taniguchi et al. |
| 4,128,590 A | 12/1978 | Pollitzer et al. |
| 4,151,071 A | 4/1979 | Myers |
| 4,420,649 A | 12/1983 | Antos |
| 4,456,631 A | 6/1984 | Crosbie et al. |
| 4,458,098 A | 7/1984 | Antos |
| 4,886,928 A | 12/1989 | Imai et al. |
| 5,308,822 A | 5/1994 | Iezzi et al. |
| 5,723,707 A | 3/1998 | Heyse et al. |
| 5,736,478 A | 4/1998 | Cortright et al. |
| 5,759,946 A | 6/1998 | Hoang et al. |
| 6,197,717 B1 | 3/2001 | Alexander et al. |
| 6,239,325 B1 | 5/2001 | Kishimoto et al. |

FOREIGN PATENT DOCUMENTS

GB  571251 A  9/1945

*Primary Examiner*—Thuan Dinh Dang
(74) *Attorney, Agent, or Firm*—Raymond F. Keller; Amin, Turocy & Calvin, LLP

(57) ABSTRACT

One aspect of the invention relates to a dehydrogenation catalyst composite containing alumina, chromium oxide, lithium oxide, and sodium oxide. The invention also relates to methods of making the dehydrogenation catalyst composite. Another aspect of the invention relates to method of dehydrogenating a dehydrogenatable hydrocarbon involving contacting the dehydrogenatable hydrocarbon with a dehydrogenation catalyst composite containing alumina, chromium oxide, lithium oxide, and sodium oxide to provide a dehydrogenated hydrocarbon, such as an olefin.

20 Claims, No Drawings

PARAFFIN DEHYDROGENATION CATALYST

RELATED APPLICATIONS

This application is a Divisional of application Ser. No. 10/170,297 filed Jun. 12, 2002, now U.S. Pat. 7,012,038 which is hereby incorporated by reference.

FIELD OF THE INVENTION

The present invention generally relates to stable, long lasting dehydrogenation catalysts with high activity. In particular, the present invention relates to catalyst composites containing alumina, chromium, and lithium.

BACKGROUND OF THE INVENTION

Catalytic methods for producing lower olefins, such as propylene and isobutylene, by dehydrogenating lower alkanes are known. Various methods include using platinum catalysts, noble metal promoted zinc aluminate spinel catalysts, or chrome-alumina catalysts. However, these catalytic processes suffer from two drawbacks. First, it is difficult to obtain high yields due to equilibrium limitations. Second, the high temperatures typically required for these processes tend to degrade the catalyst.

One type of catalyst commonly used for dehydrogenating lower alkanes is an alumina supported chromia catalyst. Although this catalyst has a relatively high dehydrogenation activity, it suffers from rapid coke formation during the dehydrogenation reaction. Consequently, frequent high temperature regeneration cycles are undesirably required. Due to the need for frequent regeneration, catalysts having a high degree of hydrothermal stability in order to prevent frequent and costly catalyst replacement are desired.

The rapid coke formation and frequent regeneration also necessitate the employment of cyclical processes, such as the Houdry process, when using chromia-alumina as a dehydrogenation catalyst. Cyclical processes make use of parallel reactors that contain a shallow bed of chromia-alumina catalyst. The feed is preheated through a fired heater before passing over the catalyst in the reactors. The hot product is cooled, compressed and sent to the product fractionation and recovery station. To facilitate continuous operation, the reactors are operated in a timed cycle. Each complete cycle typically consists of dehydrogenation, regeneration, reduction, and purge segments. A further requirement for continuous operation is the use of a parallel set of reactors, such as 3 to seven reactors. In an effort to circumvent equilibrium limitations, the reactors are operated at sub-atmospheric pressures during the dehydrogenation cycle (2 to 14 psia). Regeneration is performed with pre-heated air through a direct fire burner or with the exhaust of a gas turbine. Regeneration temperatures range from 550° C. to 700° C.

Because of such severe operating conditions, dehydrogenation catalyst life is typically one to less than two years. Catalyst replacement is performed when conversion and selectivity fall below minimum levels required for the economic operation of the unit. For example, a dehydrogenation catalyst may have an initial conversion and selectivity values of 50-60% and 88-90%, respectively, while end-of-life conversion and selectivity values are typically 40-45% and 75-85%, respectively. Improvements in dehydrogenation catalysts are desired.

Oxygenates constitute a class of gasoline additives. Since passage of the Clean Air Act Amendments of 1990, the demand for oxygenates has been increasing. The most commonly used oxygenates today are methanol, ethanol, and ethers such as methyl tertiary butyl ether (MTBE). Although methanol and ethanol have high blending octanes, problems with toxicity, water miscibility, high Reid Vapor Pressure (RVP), high nitrogen oxide emissions, lower fuel efficiency, and cost make methanol and ethanol less attractive. Consequently, MTBE is particularly attractive. Homologues of MTBE such as ethyl tertiary butyl ether (ETBE) and methyl tertiary amyl ether (TAME) are increasingly attractive.

Ether production capacity is often limited by iso-olefin feedstock availability. In this connection, MTBE and ETBE production processes both utilize isobutylene as a feedstock while TAME production processes utilize isoamylene as a feedstock. Isobutylene and isoamylene are typically supplied to an ether production process from a fluid catalytic cracking unit (FCC), a fluidized or delayed coker, or from downstream paraffin isomerization and dehydrogenation facilities. As a result, the availability of hydrocarbons having 4 or 5 carbon atoms is limited by numerous possible constraints including crude properties, FCC catalyst properties and operating conditions, coking conditions, as well as by other refinery operating constraints. The chemical mix of C4 and C5 paraffins, olefins, and aromatics as well as the particular mix of iso-olefins to normal olefins are similarly constrained.

SUMMARY OF THE INVENTION

The present invention provides dehydrogenation catalyst composites that exhibit high activity, high selectivity, robust hydrothermal stability, high yields, long catalyst life cycles, and low deactivation rates. The low deactivation rates are achievable even while operating at high temperatures. Furthermore, the dehydrogenation catalyst composites can be advantageously employed without supplemental hydrogen. The dehydrogenation catalyst composites enable the efficient manufacture of feedstocks used in the production of polyolefins such as polypropylene and gasoline additives such as MTBE.

One aspect of the invention relates to a dehydrogenation catalyst composite containing alumina, chromium oxide, lithium oxide, and sodium oxide. The invention also relates to methods of making the dehydrogenation catalyst composite.

Another aspect of the invention relates to method of dehydrogenating a dehydrogenatable hydrocarbon involving contacting the dehydrogenatable hydrocarbon with a dehydrogenation catalyst composite containing alumina, chromium oxide, lithium oxide, and sodium oxide to provide a dehydrogenated hydrocarbon, such as an olefin.

DETAILED DESCRIPTION OF THE INVENTION

The high temperature stable dehydrogenation catalyst composite (support and catalyst) in accordance with one aspect of the present invention contains alumina, lithium oxide, chromium oxide, and sodium oxide. Generally speaking, the dehydrogenation catalyst composite is made by mixing alumina and a lithium compound to form an alumina mixture, optionally heating to a first temperature, combining a chromium compound and a sodium compound with the alumina mixture, and heating to a second temperature (in the event a first heat treatment is employed). Alternatively, the dehydrogenation catalyst composite is made by mixing alumina to form an alumina mixture, optionally heating to a first temperature, combining a chromium compound, a lithium compound, and a sodium compound with the alumina mixture, and heating to a second temperature (in the event a first heat treatment is employed).

In one embodiment, alumina, a lithium compound, and optionally one or more additives are initially mixed together. In another embodiment, alumina and optionally one or more additives are initially mixed together. Specific examples of alumina that can be used include gamma-alumina, eta-alumina, theta-alumina, and the like. Examples of commercially available material include those under the trade designation Pural® (such as 200, BT, NF, NG, SB, SBI, SCC, and SCF) and Catapal® (such as A, B, and C1) from Condea Chemie GmbH and those under the trade designation Versal™ (such as B) from UOP, Inc.

The lithium compound is converted to lithium oxide during heating. The lithium compound is a molecule containing at least one atom of lithium. General examples of lithium compounds include lithium salts, organolithium compounds, lithium, and lithium oxide. Specific examples of lithium compounds include lithium metal powder, lithium acetate, lithium amide, lithium borates, lithium carbonate, lithium formate, lithium halides such as lithium fluoride, lithium chloride, lithium bromide, and lithium iodide, lithium hydride, lithium hydroxide, lithium hypochlorite, lithium nitrate, lithium nitride, lithium phosphate, lithium silicate, lithium zirconate, lithium oxide, lithium perchlorate, lithium peroxide, lithium metasilicate, lithium sulfate, lithium butyllithium, lithium methyllithium, lithium phenyllithium, and the like. While not wishing to be bound by any theory, it is believed that the subsequently formed lithium oxide stabilizes defect sites within the alumina.

The alumina and lithium compound are mixed to uniformly distribute the lithium compound in the alumina. In one embodiment, the mixture contains about 85% or more and about 99.9% or less of alumina and about 0.1% or more and about 15% or less of the lithium compound (all % s by dry weight). In another embodiment, the mixture contains about 90% or more and about 99.5% or less of alumina and about 0.5% or more and about 10% or less of the lithium compound. In yet another embodiment, the mixture contains about 95% or more and about 99% or less of alumina and about 1% or more and about 5% or less of the lithium compound. Alternatively, if the lithium compound is not initially mixed with alumina, then the mixture contains about 85% or more and about 100% or less of alumina.

The alumina mixture, whether or not the lithium compound is present, may contain optional additives such as an extrusion agent, a rheology control agent such as Methocel, binder, surface active agents, an acid, a base, clay, supplemental support materials such as silica, titania, zirconia, zinc oxide, boria, and the like. However, in one embodiment, supplemental support materials such as silica, titania, zirconia, zinc oxide, and boria are not added to the alumina mixture, and thus are not contained in the resultant catalyst composite, except in small or trace amounts.

The alumina mixture may be mixed well in a high shear mixer with water and until a rather stiff dough is obtained. This dough can be extruded and/or formed into any suitable shape including cylinders, cubes, stars, tri-lobes, quadra-lobes, pellets, pills, or spheres by suitable mechanical means. In one embodiment, mixing is conducted in a high intensity environment, such as that supplied by a Littleford Mixer available from Littleford Day, Inc., Florence, Ky. Mixing is conducted for a time sufficient so that a fine uniform mix results. In another embodiment, deionized water is added to the mixture during mixing in an amount to yield a stiff, dough-like material suitable for extrusion.

After mixing, the alumina mixture is formed or extruded into a suitable shape. The shape substantially corresponds to the shape of the resultant catalyst support. In one embodiment, the alumina mixture is extruded in a continuous manner over a broad range of diameters and shapes. Examples of forming or extrusion machines include extrusion molding machines, single screw extruders, twin screw extruders, coextruders, pin extruders, linear extruders, and monofilament extruders.

The alumina mixture is then optionally formed into any desired shape. Examples of forming machines include molding machines, tableting machines, rolling granulators, marumarizers, and pelletors. The shape of the formed alumina mixture includes spheres, tablets, cylinders, stars, tri-lobes, quadra-lobes, pellets, pills, granules, honeycombs, and cubes. The shapes, generally referred to as "particulate", may have any suitable size. However, in a preferred embodiment, the sizes of the shapes are substantially uniform. The shaped material has its components (the alumina and optionally lithium compound) mixed therein. In one embodiment, the shaped material has its components uniformly mixed therein.

After forming the material into a desired shape, the alumina mixture is optionally dried to remove any remaining liquid (and typically to remove remaining water). Drying is conducted in at least one of a desiccator, under a vacuum (reduced pressure), and/or elevated temperature (baking) for a sufficient period of time to remove any remaining liquid from the shaped material.

The manner in which the shaped alumina mixture is dried is not critical. In one embodiment, the dried alumina mixture contains less than about 3% by weight free moisture. In another embodiment, the dried alumina mixture contains less than about 1% by weight free moisture.

In one embodiment, drying involves at least one of maintaining an elevated temperature (above about 35° C.) overnight, desiccation overnight, and under a vacuum overnight. When employing elevated temperatures, in one embodiment, the shaped alumina mixture is heated from about 35° C. to about 150° C. for a time from about 5 seconds to about 6 hours.

The alumina mixture is subjected to an optional heat treatment. If this heat treatment is performed, then it is a first heat treatment. The alumina mixture is preferably heated in an oxygen containing atmosphere such as air or water vapor. If the lithium compound, alumina, and any additives are combined in a water mixture, the shaped mixture may be optionally dried before heating. In one embodiment, the heat treatment involves heating at a temperature of about 500° C. or more and about 1,000° C. or less for about 1 minute or more and about 300 minutes or less. In another embodiment, the heat treatment involves heating at a temperature of about 600° C. or more and about 900° C. or less for about 5 minutes or more and about 200 minutes or less. In yet another embodiment, the heat treatment involves heating at a temperature of about 650° C. or more and about 850° C. or less for about 10 minutes or more and about 150 minutes or less.

Although not critical to the invention, if heat treated the alumina mixture has a surface area sufficient to facilitate incorporation of a chromium compound thereon/therein. In one embodiment, the heat treated alumina mixture has a surface area of about 50 $m^2/g$ or more and about 400 $m^2/g$ or less. In another embodiment, the heat treated alumina mixture has a surface area of about 75 m²/g or more and about 300 m²/g or less. The heat treated alumina mixture, whether or not the lithium compound is present, has a porous structure throughout the shaped mixture. The porous nature of the alumina mixture facilitates incorporation of the chromium compound, lithium compound (if not already present), sodium compound, and additional additives therein during subsequent processing.

The incorporation of the chromium compound, lithium compound (if not already present), sodium compound, and additional additives into the alumina mixture occurs throughout the alumina mixture. Unlike many catalyst composites where the catalytic metal is incorporated on the outer edges of a support, the chromium compound is incorporated across the cross-sectional area of the resultant catalyst composite. That is, the chromium compound penetrates and is present throughout the alumina mixture. In one embodiment, the chromium compound is incorporated uniformly within the alumina mixture. The term uniformly is defined below.

A chromium compound is mixed with the heat treated alumina mixture. If the alumina mixture does not contain a lithium compound, then the lithium compound is included with the chromium compound. The chromium compound is a molecule containing at least one atom of chromium. The chromium compound is converted to chromium oxide during heating (one or more of chromium (III) oxide and chromium (VI) oxide). General examples of chromium compounds include chromium, chromium salts, chromates, chromic acid, and chromium oxides. Specific examples of chromium compounds include chromium, sodium chromate, sodium dichromate, potassium chromate, potassium dichromate, ammonium dichromate, chromic acid, chromic chloride, chromic acetylacetonate, chromic potassium sulfate, chromium (III) oxide, chromium (VI) oxide, barium chromate, chromyl chloride, barium chromate, strontium chromate, lead chromate, chromium nitride, chromium nitrate, chromium fluoride, and the like.

A sodium compound is mixed with the heat treated alumina mixture. The sodium compound is a molecule containing at least one atom of sodium. The sodium compound is converted to sodium oxide during heating. General examples of sodium compounds include sodium salts, sodium chromates, organosodium compounds, and sodium oxide. Specific examples of sodium compounds include sodium oxide, sodium fluoride, sodium chloride, sodium bromide, sodium iodide, sodium chromate, sodium dichromate, sodium acetate, sodium bicarbonate, sodium carbonate, sodium formate, sodium hydroxide, sodium metasilicate, sodium nitrate, sodium nitrite, sodium phosphate, sodium sulfate, sodium sulfite, and the like. In one embodiment, the sodium compound and the chromium compound are the same compound, such as sodium chromate or sodium dichromate.

The alumina mixture, chromium compound, lithium compound (if not in the alumina mixture), and sodium compound are combined, preferably with water, and more preferably with deionized water, and mixed so that the chromium compound, lithium compound (if not in the alumina mixture), and sodium compound are distributed around/in the alumina mixture (not just in the surface pores) due, in part, to the porous nature of the alumina mixture as a whole. The water is then removed, by at least one of reduced pressure and gentle heating.

After the alumina mixture, chromium compound, lithium compound (if not in the alumina mixture), and sodium compound are combined, optional drying is conducted to remove any remaining liquid (and typically to remove remaining water). Drying is conducted in at least one of a desiccator, under a vacuum (reduced pressure), and/or elevated temperature (baking) for a sufficient period of time to remove any remaining liquid. When employing elevated temperatures, in one embodiment, heating is conducted from about 35° C. to about 150° C. for a time from about 5 minutes to about 10 hours.

The manner in which the catalyst combination is dried is not critical. In one embodiment, the dried catalyst combination contains less than about 3% by weight free moisture. In another embodiment, the dried catalyst combination contains less than about 1% by weight free moisture.

The catalyst combination is subjected to a heat treatment. If the optional heat treatment is previously performed, then this is a second heat treatment. The catalyst combination is preferably heated in an oxygen containing atmosphere such as air or water vapor. In one embodiment, the heat treatment involves heating at a temperature of about 500° C. or more and about 900° C. or less for about 1 minute or more and about 400 minutes or less. In another embodiment, the heat treatment involves heating at a temperature of about 550° C. or more and about 800° C. or less for about 5 minutes or more and about 300 minutes or less. In yet another embodiment, the heat treatment involves heating at a temperature of about 600° C. or more and about 750° C. or less for about 10 minutes or more and about 150 minutes or less. If a first and a second heat treatment are employed, the first heat treatment is higher than the second heat treatment.

In one embodiment, the resultant catalyst composite contains about 60% or more and about 95% or less of alumina, about 5% or more and about 30% or less of chromium oxide, about 0.01% or more and about 5% or less of lithium oxide, about 0.01% or more and about 5% or less of sodium oxide, (all %s by weight). In another embodiment, the catalyst composite contains about 70% or more and about 90% or less of alumina, about 10% or more and about 25% or less of chromium oxide, about 0.05% or more and about 3% or less of lithium oxide, about 0.05% or more and about 3% or less of sodium oxide. In yet another embodiment, the catalyst composite contains about 75% or more and about 85% or less of alumina, about 15% or more and about 22% or less of chromium oxide, about 0.1% or more and about 1% or less of lithium oxide, about 0.1% or more and about 1% or less of sodium oxide.

In one embodiment, the catalyst composite contains a porous alumina-lithium oxide matrix with chromium oxide and sodium oxide uniformly incorporated in/on the pores of the alumina-lithium oxide matrix. This orientation is obtained when the lithium compound is initially mixed with alumina to form the alumina mixture. In another embodiment, the catalyst composite contains a porous alumina matrix with chromium oxide, lithium oxide, and sodium oxide uniformly incorporated in/on the pores of the alumina oxide matrix. This orientation is obtained when the lithium compound is added with the chromium compound and sodium compound to the alumina mixture (that does not contain a lithium compound). However, a lithium compound may be initially mixed with alumina to form the alumina mixture and added with the chromium compound and sodium compound to the alumina mixture. In this embodiment, the catalyst composite contains a porous alumina-lithium oxide matrix with chromium oxide, lithium oxide, and sodium oxide uniformly incorporated in/on the pores of the alumina-lithium oxide matrix.

The uniformity of chromium distribution throughout the catalyst composite can be assessed using a "chromium mapping" technique. This is performed through the use of a scanning electron microscope equipped with a wavelength dispersive x-ray detector. For example, a Hitachi S-3500 N microscope may be employed. As the detector scans across an individual catalyst composite pellet, it generates a number of x-ray counts which is proportional to the concentration of chromium in a given position in the pellet. The number of counts recorded in the center of pellet is compared with that recorded from the outer edge locations.

In one embodiment, when the number of counts recorded in the center of pellet is within 30% of that recorded from the outer edge locations, the chromium is uniformly distributed throughout the catalyst composite. In another embodiment, when the number of counts recorded in the center of pellet is within 20% of that recorded from the outer edge locations, the chromium is uniformly distributed throughout the catalyst composite. In another embodiment, when the number of counts recorded in the center of pellet is within 10% of that recorded from the outer edge locations, the chromium is uniformly distributed throughout the catalyst composite.

The catalyst composite has a ratio of chromium oxide to lithium oxide that promotes stability and/or a low deactivation rate, and/or facilitates the catalytic dehydrogenation process. In one embodiment, the ratio of chromium oxide to lithium oxide in the dehydrogenation catalyst composite is from about 1:1 to about 500:1 (on a weight basis). In another embodiment, the ratio of chromium oxide to lithium oxide in the dehydrogenation catalyst composite is from about 2:1 to about 100:1. In another embodiment, the ratio of chromium oxide to lithium oxide in the dehydrogenation catalyst composite is from about 5:1 to about 20:1.

The resultant catalyst composite optionally contains additives that promote stability and/or a low deactivation rate, and/or facilitate the catalytic dehydrogenation process. Examples of additives include surface active agents, binders, and the like. In one embodiment, the resultant catalyst composite contains about 0.01% or more and about 10% or less of an optional additive (all %s by weight). In another embodiment, the resultant catalyst composite contains about 0.05% or more and about 5% or less of an optional additive. These additives can be initially mixed with the alumina and lithium compound, and/or mixed with the lithium-alumina mixture along with the chromium compound.

In one embodiment, the catalyst composite of the present invention does not contain one or more of nickel, platinum, palladium, and zinc. In these embodiments, under some conditions one or more of nickel, platinum, palladium, and zinc may detrimentally effect the dehydrogenation reaction. In another embodiment, the catalyst composite of the present invention contains one or more of nickel, platinum, and palladium.

The resultant catalyst composite has a surface area sufficient to facilitate dehydrogenation reactions. In one embodiment, the catalyst composite has a surface area of about 30 m$^2$/g or more and about 300 m$^2$/g or less. In another embodiment, the catalyst composite has a surface area of about 50 m$^2$/g or more and about 250 m$^2$/g or less. In yet another embodiment, the catalyst composite has a surface area of about 70 m$^2$/g or more and about 200 m$^2$/g or less.

The catalyst composite of the present invention is contacted with feedstock under suitable conditions to facilitate a dehydrogenation reaction. For example propane is used as a feedstock to produce propylene and isobutane is used as a feedstock to produce isobutylene. General examples of feedstock materials (dehydrogenatable hydrocarbons) include aliphatic compounds containing about 2 or more and about 30 or less carbon atoms per molecule, alkylaromatic hydrocarbons where the alkyl group contains about 2 or more and about 6 or less carbon atoms, and naphthenes or alkyl-substituted naphthenes where the alkyl group contains about 2 or more and about 6 or less carbon atoms. Specific examples of dehydrogenatable hydrocarbons include ethane, propane, n-butane, isobutane, n-pentane, isopentane, n-hexane, 2-methylpentane, 3-methylpentane, 2,2-dimethylbutane, n-heptane, 2-methylhexane, 2,2,3-trimethylbutane, cyclopentane, cyclohexane, methylcyclopentane, ethylcyclopentane, n-propylcyclopentane, 1,3-dimethylcyclohexane, ethylbenzene, n-butylbenzene, 1,3,5-triethylbenzene, isopropylbenzene, isobutylbenzene, ethylnaphthalene, and the like.

Generally speaking, the feedstocks suitable for use with the present invention generally contain paraffinic hydrocarbons having about 2 or more and about 20 or less carbon atoms. In another embodiment, the feedstocks contain paraffinic hydrocarbons having about 3 or more and about 12 or less carbon atoms. In one embodiment, the feedstocks boil at a temperature of about 400° C. or less at atmospheric pressure. In another embodiment, the feedstocks boil at a temperature of about 250° C. or less at atmospheric pressure.

In one specific embodiment, a catalytic process is provided for dehydrogenating hydrocarbons for direct or eventual upgrade to ethers such as, but not limited to, MTBE, ETBE, and TAME. Feedstocks for use with the present invention and suitable for providing etherification feedstocks generally comprise aliphatic or alicyclic hydrocarbons having about 3 or more and about 7 or less carbon atoms. Since most etherification processes convert iso-olefins to ethers, the feedstock to such processes may require isomerization prior to etherification. The present invention can effectively dehydrogenate isoparaffins as well as normal paraffins therefore providing the flexibility to incorporate the process upstream, downstream or concurrent with an isomerization step.

In another specific embodiment, a process is provided for dehydrogenating hydrocarbons for improving gasoline research and/or motor octane. An olefinic hydrocarbon boiling in the gasoline or naphtha boiling point temperature range has a higher research and motor octane than its paraffinic counterparts. At least a portion of such feedstocks generally contain paraffinic hydrocarbons having about 3 or more and about 12 or less carbon atoms and the paraffinic hydrocarbon can be normal, branched, or a combination thereof.

In yet another specific embodiment, a process is provided to dehydrogenate hydrocarbons for use as feed to a petroleum refinery alkylation process. Feedstocks suitable for dehydrogenation for providing alkylation unit feedstock typically contain paraffinic hydrocarbons having about 2 or more and about 6 or less carbon atoms. In another embodiment, the feedstocks for providing alkylation unit feedstock contain paraffinic hydrocarbons having about 3 or more and about 5 or less carbon atoms including about 4 carbon atoms. The paraffinic fraction of such feedstocks can be normal, branched, or a combination thereof.

In still yet another specific embodiment, a process is provided to dehydrogenate hydrocarbons for use as feed for commercial chemical manufacture. Feedstocks having about 3 or more and about 5 or less carbon atoms are dehydrogenated into olefinic feedstocks for the subsequent production of polyethylene, polypropylene, polybutylene, polyisobutlyene, or other chemical compositions that are commonly sold in solid or liquid forms.

The feedstocks can be processed through the catalytic processes of the present invention neat or can be combined with recycled portions of the product stream from the dehydrogenation process. Similarly, combinations of the above-described feedstock embodiments can be directed to the catalytic processes of the present invention and the products subsequently fractionated to individual product pools. The catalytic processes of the present invention can also be operated in "blocked out" mode where only one feedstock is processed through the facility at any one time.

The dehydrogenation process of the present invention optionally begins with preheating a hydrocarbon feedstock. The feedstock can be preheated in feed/reactor effluent heat exchangers prior to entering a furnace or contacting other high temperature waste heat as a means for final preheating to a targeted catalytic reaction zone inlet temperature. Suitable final preheating means include, for example, waste heat from other refinery processes such as a fluid catalytic cracking unit, a fluidized or delayed coking unit, a catalytic hydrocracker, a crude distillation unit, a catalytic reforming unit, and/or hydrotreating units found in conventional petroleum refineries.

The reaction zone can include one or more fixed bed reactors containing the same or different catalysts, a moving bed reactor, or a fluidized bed reactor. The feedstock may be contacted with the catalyst bed in either upward, downward, or radial flow fashion. The reactants may be in the liquid phase, mixed liquid and vapor phase, or the vapor phase.

In embodiments where a fixed bed reactor is employed, a dehydrogenation reaction zone may contain one or at least two fixed bed reactors. Fixed bed reactors in accordance with the present invention can also comprise a plurality of catalyst beds. The plurality of catalyst beds in a single fixed bed reactor can also comprise the same or different catalysts.

Since dehydrogenation reactions are generally endothermic, interstage heating, consisting of heat transfer devices between fixed bed reactors or between catalyst beds in the same reactor shell, can be employed. Heat sources can include conventional process heaters such as one or more process furnaces or can include internally produced heat such as that produced from catalyst regeneration within a fluidized catalytic process. Heating requirements may also be met from heating sources available from other refinery process units.

The dehydrogenation reaction zone effluent is generally cooled and the effluent stream is directed to a separator device such as a stripper tower where light hydrocarbons and hydrogen formed during the reaction step can be removed and directed to more appropriate hydrocarbon pools. Where the process is performed in the presence of supplemental hydrogen or sufficient internally generated hydrogen is produced, a separate hydrogen separation step can be performed upstream of and prior to light hydrocarbon separation. Some of the recovered hydrogen can be recycled back to the process while some of the hydrogen can be purged to external systems such as plant or refinery fuel.

The stripper liquid effluent product is then generally conveyed to downsteam processing facilities. The olefin product optionally can be directed to a polymerization facility or to an isomerization process for isomerization and thereafter directed to an ether facility for conversion, in the presence of an alkanol, to an ether. Where at least a portion of the olefin from the process of the present invention is iso-olefin, the stream can be sent directly to an ether facility or to a polymerization facility. Prior to direction to an ether facility, the product stream can be purified by removing unconverted paraffinic hydrocarbon from the product. This unconverted product can be recycled back to the reaction zone or further manipulated in other process units. The olefin product can be directed to an alkylation process for reaction with isoparaffin to form higher octane, lower volatility gasoline blending components. The olefin product can be directed to a chemical manufacture process for conversion to other commodity chemical products or process streams. Methods for integration of the process of the present invention with other conventional refinery or chemical plant processes or products are known to those skilled in the art.

The catalyst composite is used at a temperature to facilitate catalytic dehydrogenation processes. In one embodiment, the temperature during catalytic dehydrogenation is about 250° C. or higher and about 700° C. or lower. In another embodiment, the temperature during catalytic dehydrogenation is about 400° C. or higher and about 650° C. or lower. Reaction temperatures below these ranges can result in reduced paraffin conversion and lower olefin yield. Reaction temperatures above these ranges can result in reduced olefin selectivity and lower olefin yields.

The catalyst composite is used at a pressure to facilitate catalytic dehydrogenation processes. In one embodiment, the pressure during catalytic dehydrogenation is about 0 psia (vacuum pressure) or more and about 500 psia or less. In another embodiment, the pressure during catalytic dehydrogenation is about 2 psia or more and about 20 psia or less. In another embodiment, the pressure during catalytic dehydrogenation is about 20 psia or more and about 300 psia or less. Excessively high reaction pressures increase energy and equipment costs and provide diminishing marginal benefits. Excessively high hydrogen circulation rates can also influence reaction equilibrium and drive the reaction undesirably towards reduced paraffin conversion and lower olefin yield.

The catalyst composite is used at a weight hourly space velocity (WHSV) to facilitate catalytic dehydrogenation processes. In one embodiment, the WHSV is about 0.1 hr$^{-1}$ or more and about 100 hr$^{-1}$ or less. In another embodiment, the WHSV is about 0.5 hr$^{-1}$ or more and about 50 hr$^{-1}$ or less. Feed space velocities exceeding the levels described herein generally result in a decline in paraffin conversion which overwhelm any gain in olefin selectivity, thereby resulting in lower olefin yield. Feed space velocities short of the levels described herein are generally costly in terms of capital requirements.

The dehydrogenation catalyst composite and process of the present invention provides superior overall dehydrogenation properties including one or more of high selectivity, high activity, low deactivation rate, high yields, and the like. In one embodiment, the dehydrogenation catalyst composites of the present invention can achieve paraffin conversion levels of about 50% or more. In another embodiment, the dehydrogenation catalyst composites can achieve paraffin conversion levels of about 60% or more. In one embodiment, the dehydrogenation catalyst composites of the present invention can achieve olefin selectivity levels of about 85% or more. In another embodiment, the dehydrogenation catalyst composites can achieve olefin selectivity levels of about 92% or more. In one embodiment, the dehydrogenation catalyst composites of the present invention can achieve olefin yield levels of about 40% or more. In another embodiment, the dehydrogenation catalyst composites can achieve olefin yield levels of about 50% or more.

The dehydrogenation catalyst and process of the present invention provides the above-described levels of performance while resisting catalyst deactivation, thereby extending catalyst cycle life under dehydrogenation conditions. This is due, in part, to the relatively high hydrothermal stability possessed by the dehydrogenation catalyst composites. In one embodiment, the dehydrogenation catalyst composites of the present invention have olefin yield deactivation loss levels of about 5% or less over a period of 200 days. In another embodiment, the dehydrogenation catalyst composites have olefin yield deactivation loss levels of about 2% or less over a period of 200 days. In yet another embodiment, the dehydrogenation catalyst composites have olefin yield deactivation loss levels of about 1% or less over a period of 200 days.

In one embodiment, the dehydrogenation catalyst composites of the present invention can be employed in olefin production without a substantial loss of yield (less than 5%) for about 200 days or more. In another embodiment, the dehydrogenation catalyst composites can be employed in olefin production without a substantial loss of yield for about 250 days or more. In another embodiment, the dehydrogenation catalyst composites can be employed in olefin production without a substantial loss of yield for about 300 days or more. In one embodiment, end-of-life conversion and selectivity values are reached after about 2 or more years of use. In one embodiment, end-of-life conversion and selectivity values are reached after about 2.5 or more years of use.

General examples of dehydrogenated hydrocarbons that are catalytically made from the feedstock materials include olefin compounds containing about 2 or more and about 30 or less carbon atoms per molecule, alkenylaromatic hydrocarbons where the alkenyl group contains about 2 or more and about 6 or less carbon atoms, and naphthenes or alkenyl-substituted naphthenes where the alkenyl group contains about 2 or more and about 6 or less carbon atoms. Specific examples of dehydrogenated hydrocarbons include ethylene, propylene, butene, isobutylene, pentene, isopentene, hexene, 2-methylpentene, 3-methylpentene, 2,2-dimethylbutene, heptene, 2-methylhexene, 2,2,3-trimethylbutene, cyclopentene, cyclohexene, methylcyclopentene, ethylcyclopentene, n-propylcyclopentene, propylenylpentane, 1,3-dimethylcyclohexene, styrene, butenylbenzene, triethenylbenzene, methylstyrene, isobutenylbenzene, ethenylnaphthalene, and the like.

The following examples illustrate the present invention. Unless otherwise indicated in the following examples and elsewhere in the specification and claims, all parts and percentages are by weight, all temperatures are in degrees Centigrade, and pressure is at or near atmospheric pressure.

EXAMPLE 1

Alumina (1076.9 g), lithium nitrate (10.3 g), 70% nitric acid (50 g), and deionized water (170 g) are mixed for 10-15 minutes. The mixture is extruded into ⅛ inch cylinders and permitted to air dry overnight. The cylinders are dried in an oven at 120° C. for 24 hours, then cooled to room temperature. The cylinders are then heated at 850° C. for 60 minutes. The cylinders (300 g), sodium bichromate dihydrate (10.3 g), chromium (VI) oxide (98.8 g), and deionized water (109 g) are combined, mixed, heated at 40° C. for 75 minutes, and at 60° C. for 30 minutes. The water is then evaporated. The cylinders are placed in an oven to dry for 2 hours at 120° C. The cylinders are heated at 660° C. for 120 minutes.

EXAMPLE 2

Alumina (1076.9 g), 70% nitric acid (50 g), and deionized water (170 g) are mixed for 10-15 minutes. The mixture is extruded into ⅛ inch cylinders and permitted to air dry overnight. The cylinders are dried in an oven at 120° C. for 24 hours, then cooled to room temperature. The cylinders are then heated at 850° C. for 60 minutes. The cylinders (300 g), sodium bichromate dihydrate (10.3 g), lithium nitrate (10.3 g), chromium (VI) oxide (98.8 g), and deionized water (109 g) are combined, mixed, heated at 40° C. for 75 minutes, and at 60° C. for 30 minutes. The water is then evaporated. The cylinders are placed in an oven to dry for 2 hours at 120° C. The cylinders are heated at 660° C. for 120 minutes.

The dehydrogenation of dehydrogenatable hydrocarbons is an important commercial process because of the high and diverse demand for dehydrogenated hydrocarbons for use in the manufacture of various chemical products such as detergents, plastics, synthetic rubbers, pharmaceutical products, high octane gasoline, perfumes, drying oils, ion-exchange resins, and various other products well known to those skilled in the art. One example of this demand is in the manufacture of high octane gasoline by using C3 and C4 mono-olefins to alkylate isobutane. Another example of this demand is in the area of dehydrogenation of normal paraffin hydrocarbons to produce normal mono-olefins having from about 3 to about 30 carbon atoms per molecule. These normal mono-olefins can, in turn, be utilized in the synthesis of a vast number of other chemical products. Regarding the use of products made by the dehydrogenation of alkylaromatic hydrocarbons, they find wide application in the petroleum, petrochemical, pharmaceutical, detergent, plastic, and other industries.

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A method of dehydrogenating a dehydrogenatable hydrocarbon comprising:
   contacting the dehydrogenatable hydrocarbon with a dehydrogenation catalyst composite comprising about 60% or more and about 95% by weight or less of alumina, about 5% or more and about 30% by weight or less of chromium oxide, about 0.1% or more and about 1% by weight or less of lithium oxide, and about 0.01% or more and about 5% by weight or less of sodium oxide to provide a dehydrogenated hydrocarbon.

2. The method of claim 1, wherein the dehydrogenatable hydrocarbon comprises at least one selected from the group consisting of aliphatic compounds containing about 2 or more and about 30 or less carbon atoms per molecule, alkylaromatic hydrocarbons where the alkyl group contains about 2 or more and about 6 or less carbon atoms, and alkyl-substituted naphthenes where the alkyl group contains about 2 or more and about 6 or less carbon atoms.

3. The method of claim 1, wherein the dehydrogenatable hydrocarbon comprises at least one selected from the group consisting of ethane, propane, n-butane, isobutane, n-pentane, isopentane, n-hexane, 2-methylpentane, 3-methylpentane, 2,2-dimethylbutane, n-heptane, 2-methylhexane, 2,2,3-trimethylbutane, cyclopentane, cyclohexane, methylcyclopentane, ethylcyclopentane, n-propylcyclopentane, 1,3-dimethylcyclohexane, ethylbenzene, n-butylbenzene, 1,3,5-triethylbenzene, isopropylbenzene, isobutylbenzene, and ethylnaphthalene.

4. The method of claim 1, wherein the dehydrogenated hydrocarbon comprises at least one selected from the group consisting of olefin compounds containing about 2 or more and about 30 or less carbon atoms per molecule, alkenylaromatic hydrocarbons where the alkenyl group contains about 2 or more and about 6 or less carbon atoms, and alkenyl-substituted naphthenes where the alkenyl group contains about 2 or more and about 6 or less carbon atoms.

5. The method of claim 1, wherein the dehydrogenatable hydrocarbon comprises propane or isobutane and the dehydrogenated hydrocarbon comprises propylene or isobutylene.

6. The method of claim 1, wherein the dehydrogenatable hydrocarbon is contacted with the dehydrogenation catalyst composite at a temperature of about 250° C. or higher and about 700° C. or lower and a pressure of about 0 psia or more and about 500 psia or less.

7. The method of claim 1, wherein the dehydrogenation catalyst composite is positioned in one of a fixed bed reactor, a moving bed reactor, or a fluidized bed reactor.

8. The method of claim 1, wherein the dehydrogenation catalyst composite has a ratio of chromium oxide to lithium oxide is from about 2:1 to about 100:1.

9. The method of claim 1, wherein the dehydrogenatable hydrocarbon is contacted with the dehydrogenation catalyst composite continuously for about 2 years or more before end-of-life conversion and selectivity values are reached.

10. The method of claim 1, wherein the chromium oxide, lithium oxide, and sodium oxide are uniformly incorporated into a porous matrix of alumina.

11. The method of claim 1, wherein the chromium oxide and sodium oxide are uniformly incorporated into a porous matrix of alumina and lithium oxide.

12. A method of dehydrogenating a dehydrogenatable hydrocarbon comprising:
contacting the dehydrogenatable hydrocarbon with a dehydrogenation catalyst composite comprising about 60% or more and about 95% by weight or less of alumina, about 5% or more and about 30% by weight or less of chromium oxide, about 0.1% or more and about 1% by weight or less of lithium oxide, and about 0.01% or more and about 5% by weight or less of sodium oxide at a temperature of about 250° C. or higher and about 700° C. or lower to provide a dehydrogenated hydrocarbon.

13. The method of claim 12, wherein the dehydrogenatable hydrocarbon comprises at least one selected from the group consisting of aliphatic compounds containing about 2 or more and about 30 or less carbon atoms per molecule, alkylaromatic hydrocarbons where the alkyl group contains about 2 or more and about 6 or less carbon atoms, and alkyl-substituted naphthenes where the alkyl group contains about 2 or more and about 6 or less carbon atoms.

14. The method of claim 12, wherein the dehydrogenatable hydrocarbon is contacted with the dehydrogenation catalyst composite at a temperature of about 400° C. or higher and about 650° C. or lower and a pressure of about 0 psia or more and about 500 psia or less.

15. The method of claim 12, wherein the dehydrogenatable hydrocarbon is contacted with the dehydrogenation catalyst composite at a weight hourly space velocity of about 0.1 $hr^{-1}$ or more and about 100 $hr^{-1}$ or less to facilitate catalytic dehydrogenation.

16. The method of claim 12, wherein the dehydrogenatable hydrocarbon is contacted with the dehydrogenation catalyst composite continuously for about 2 years or more before end-of-life conversion and selectivity values are reached.

17. A method of dehydrogenating a dehydrogenatable hydrocarbon comprising:
contacting the dehydrogenatable hydrocarbon comprising about 3 or more and about 12 or less carbon atoms with a dehydrogenation catalyst composite comprising about 60% or more and about 95% by weight or less of alumina, about 5% or more and about 30% by weight or less of chromium oxide, about 0.1% or more and about 1% by weight or less of lithium oxide, and about 0.01% or more and about 5% by weight or less of sodium oxide to provide a dehydrogenated hydrocarbon.

18. The method of claim 17, wherein the dehydrogenatable hydrocarbon comprises propane or isobutane and the dehydrogenated hydrocarbon comprises propylene or isobutylene.

19. The method of claim 17, wherein the dehydrogenatable hydrocarbon is contacted with the dehydrogenation catalyst composite at a temperature of about 250° C. or higher and about 700° C. or lower and a pressure of about 0 psia or more and about 500 psia or less.

20. The method of claim 17, wherein the dehydrogenation catalyst composite is positioned in one of a fixed bed reactor, a moving bed reactor, or a fluidized bed reactor.

* * * * *